US00PP17253P3

(12) United States Plant Patent
Abrams

(10) Patent No.: US PP17,253 P3
(45) Date of Patent: Dec. 5, 2006

(54) ***GERANIUM* PLANT NAMED 'LAVENDER DOT'**

(50) Latin Name: *Pelargonium×hortorum*
Varietal Denomination: Lavender Dot

(75) Inventor: Laura B. Abrams, Sudbury, MA (US)

(73) Assignee: JP Bartlett Co Inc, Sudbury, MA (US)

( * ) Notice: Subject to any disclaimer, the term of this patent is extended or adjusted under 35 U.S.C. 154(b) by 110 days.

(21) Appl. No.: 10/950,297

(22) Filed: Sep. 27, 2004

(65) Prior Publication Data

US 2006/0070156 P1 Mar. 30, 2006

(51) Int. Cl.
*A01H 5/00* (2006.01)

(52) U.S. Cl. ..... Plt./329

(58) Field of Classification Search ..... Plt./329, Plt./330
See application file for complete search history.

*Primary Examiner*—Wendy Haas

(57) ABSTRACT

This invention is a new and distinct cultivar of a zonal *geranium* (*Pelargonium×hortorum*) named 'Lavender Dot' the cultivar has a brilliant array of colors within the plant's light lavender pink blossom and dark green foliage on a stable, full, well branched plant.

1 Drawing Sheet

Botanical designation: *Pelargonium×hortorum.*
Variety denomination: 'Lavender Dot'.
Botanical classification/cultivar designation: *Pelargonium×hortorum* cultivar 'Lavender Dot'.

BACKGROUND OF THE INVENTION

The cultivar was developed from a controlled breeding program conducted in Sudbury, Mass. The company used a non-patented cultivar designated 'Puritan 2' as the male parent and a non-patented cultivar designated 'Quaker' as the female parent in a cultivated area to create a single plant 'Lavender Dot'. 'Lavender Dot's' plant habit is symmetrical with excellent branching. Asexual propagation of the new cultivar by cuttings at the location previously stated has shown that the unique features of this new *geranium* are stable and that the plant reproduces true to type in successive generations of asexual propagation.

SUMMARY OF THE INVENTION

The plants growth habit is compact to medium in vigor. It is a full plant that performs well in both a greenhouse and in a natural environment such as a garden. It will grow more compact under drier conditions but has the ability to be a larger and more vigorous plant with sufficient water and partial shade. The blossoms are tolerant to rain, not turning brown and rotting after a day or so of straight rain. 'Lavender Dot' buds early and is consistent with a large and longer lasting blossom than many other cultivars known to inventor.

On average, the plant itself can get to over 309 millimeters tall, not including the stem or flower. The free branching nature of 'Lavender Dot' allows the plants girth to grow and flourish. The width of a single plant is measured to be 495 millimeters and growing. The striking two tone blossom color and dark green leaf color separates itself from any other known to inventor. The semi-double blossom is a light lavener pink with a darker pink to each petal. 'Lavender Dot's' stem is a distinguished light green, while the leaf produces a unique variation of colors all in its own. 'Lavender Dot's' standout performance is regarded highly due to it's excellent growth habit, size, blossom and leaf.

The new cultivar of the present invention is being marketed under the BARTLETT'S trademark.

BRIEF DESCRIPTION OF THE PHOTOGRAPH

Accompanying this application is a photographed picture of the plant and its' aspects.

Figure 1:
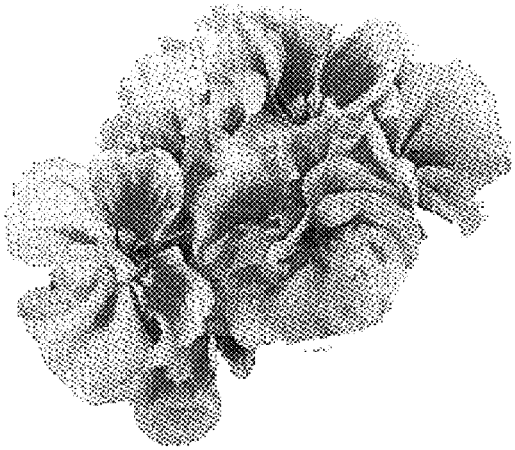

1. FIG. 1 shows the large, semi-double blossom and the purple/violet color described in the summary.

Figure 2:
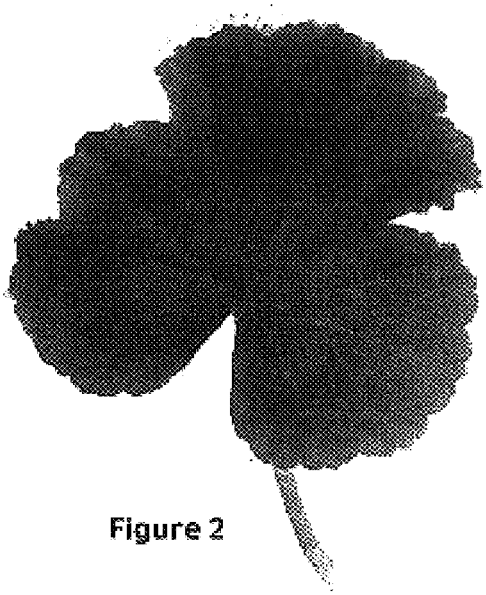

2. FIG. 2 enables us to see the medium green leaf with the medium green zone.

Figure 3:
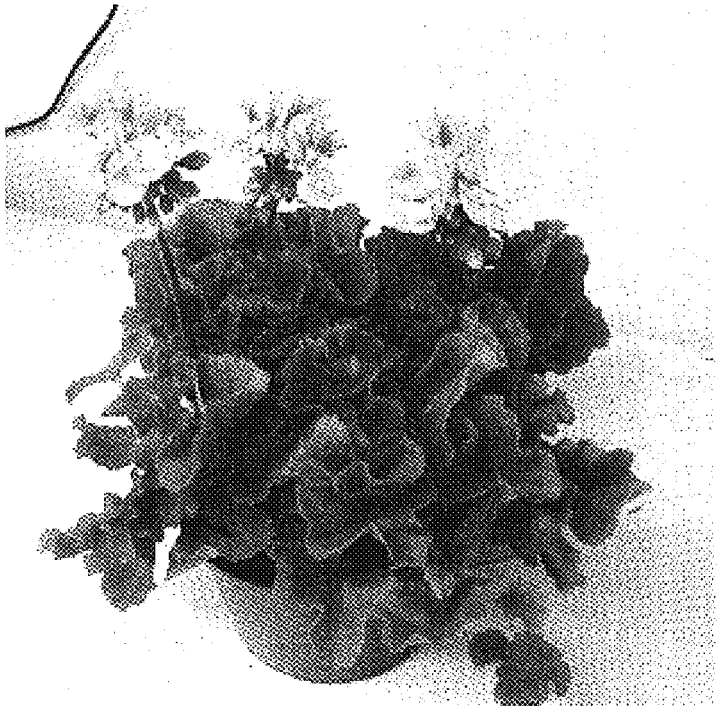

3. FIG. 3 shows the overall plant. This is a single plant from a cutting in a four-inch pot. The height, width, and growth habit are clearly seen here.

DETAILED BOTANICAL DESCRIPTION

The following observations and measurements describe asexual reproductions of 'Lavender Dot' grown in greenhouses located in Sudbury, Mass., USA. The plant history was taken on 3 month old plants grown in 7.5" pots, blossomed under natural light in a greenhouse and color readings were taken in the greenhouse in Sudbury, Mass. under ambient light. Color references are primarily to the Pantone Color Selector Chart 1000/coated 1995. The color values were determined on Oct. 22, 2003 under natural light conditions of 200 foot-candles.

Classification:
Botanical: *Pelargonium×hortorum* cv. 'Lavender Dot'.
Inflorescence:
A. Umbel:
*Flowering duration.*—The flowers last approximately 15 to 20 days under standard greenhouse conditions and then dehisce.
*Average diameter.*—Approximately 9 to 11.25 cm.
*Average depth.*—Approximately 4.9 to 6.7 cm.
*Peduncle length.*—Approximately 14.5 to 16.3 cm.
*Peduncle diameter.*—Approximately 0.05 to 0.07 cm.

*Pedicel length.*—Approximately 2.7 to 3.1 cm.

*Number of umbels per plant.*—When grown in a 7.5" pot at 8 weeks after the sticking of a rooted cutting, there commonly are approximately 7 to 9 umbels per plant. The umbels form approximately 12 to 15 cm above the foliage.

*Number of florets/umbels.*—When grown in a 7.5" pot at 8 weeks, approximately 21 to 23 florets per umbel commonly are formed.

*Flower depth.*—Approximately 6.5 to 7.3 cm.

B. Corolla:

*Buds.*—Elliptical to round in configuration, initially light green and changing to light pink at the time of opening, and approximately 11 to 14 mm. in length and approximately 5 to 7 mm. in width.

*Pedicels.*—Commonly approximately 4.5 to 6 cm in length and curved which commonly causes the buds to point substantially downward.

*Average diameter.*—Approximately 4 to 6 cm.

*Form.*—Commonly semi-double with at least two petaloids.

*Petals.*—Spatulate shaped, satiny and smooth. Commonly approximately 9 to 11 petals are present per floret. Petal base is V-shaped with a semi-circular margin. Petal length is approximately 1.8 cm and diameter is approximately 1.6 cm. Upper petal surface is smooth opposed to lower petal surface being slightly rougher.

*Number of petaloids.*—Commonly forms approximately 2 to 5 petaloids per floret. The petaloids are exactly the same as the petal except the diameter is approximately 0.4 cm.

*Color.*—General tonality from a distance of three meters: light pink with dark pink center.

*Color of upper petals surface.*—Pantone 1895C.

*Color of lower petals surface.*—Pantone 196C.

*Markings of upper petals.*—Dark pink spot at base of petal Pantone 1915C.

*Sepals.*—5 to 7 sepals per floret with a length of approximately 0.3 to 0.8 cm and width of 0.04 to 0.08 cm. The overall shape is elliptical with V-shaped base and margin and semi-circular apex. Upper and lower surface are the same texture and color, smooth, non-glossy with both Pantone 364C. Overall appearance of color is Pantone 1895C.

C. Reproductive organs:

*Androecium.*—5 fertile anthers, with whitish filaments, orange pollen the lower side of the mature (open) anther. The surface of the anther under the pollen is dark brown.

*Gynoecium.*—5 lobed pale pink stigma, Pantone 182C, greenish style, Pantone 366C; one pistil, Pantone 367C per flower.

*Fertility/seed set.*—Commonly does not produce fruits in the absence of mechanical fertilization.

*Spring flowering response period.*—Approximately 5 to 8 weeks from rooted cuttings under standard greenhouse conditions.

*Outdoor flower production.*—Freely flowering under outdoor growing conditions with substantially continuous blooming.

*Durability.*—Ships well.

*Pest/disease resistance/susceptibility.*—No susceptibility to pests or diseases noted to date. Disease resistance has not been tested to date.

Plant:

A. Foliage: Medium green with slight zonation. Zoning color is Pantone 357C. The leaves are pubescent on the upper surface, and smooth on the lower surface.

*Length.*—3.5 to 4.2 cm.

*Width.*—5.2 to 6.1 cm.

*Form.*—Reniform, with a cordate base.

*Margin.*—Irregularly crenate.

*Ribs and veins.*—Palmate 5 .1 to 5.9 cm. long.

*Leaf color.*—Upper side is Pantone 364C. Under side is Pantone 363C. Leaf upper surface covered predominately with trichomes and leaf surface is predominately smooth.

*Petioles.*—Commonly approximately 2.5 to 5 cm long with a diameter of 0.04 to 0.06 cm, Petiole color is Pantone 363C.

A. General appearance and form:

*Internode length.*—Commonly varies from approximately 0.6 to 0.9 cm.

*Branching pattern.*—Freely basal branching as well as lateral branching. No pinching is required to obtain self-branching. A self-branching growth habit is observed in the absence of a growth regulator.

*Height.*—Approximately 19 to 24 cm. above a 7.5" pot at 8 weeks under standard greenhouse conditions.

What is claimed is:

1. A new and distinct variety of *geranium* plant as herein illustrated and described.

* * * * *